(12) United States Patent
Matsumura et al.

(10) Patent No.: US 8,647,718 B2
(45) Date of Patent: Feb. 11, 2014

(54) WET LUBRICANT SURFACE COATING HAVING EXCELLENT DURABILITY, METHOD FOR SURFACE COATING, AND A MEDICAL DEVICE HAVING THE SURFACE COATING

(75) Inventors: Yoichi Matsumura, Settsu (JP); Shuhei Taniguchi, Settsu (JP)

(73) Assignee: Kaneka Corporation, Osaka (JP)

( * ) Notice: Subject to any disclaimer, the term of this patent is extended or adjusted under 35 U.S.C. 154(b) by 1017 days.

(21) Appl. No.: 11/908,394

(22) PCT Filed: Mar. 8, 2006

(86) PCT No.: PCT/JP2006/304460
§ 371 (c)(1),
(2), (4) Date: Sep. 11, 2007

(87) PCT Pub. No.: WO2006/095766
PCT Pub. Date: Sep. 14, 2006

(65) Prior Publication Data
US 2009/0270291 A1    Oct. 29, 2009

(51) Int. Cl.
*B05D 1/36* (2006.01)
*A61M 25/00* (2006.01)

(52) U.S. Cl.
USPC ......... 427/407.1; 424/422; 424/423; 604/265

(58) Field of Classification Search
USPC ...................................... 508/386; 427/407.1
See application file for complete search history.

(56) References Cited

U.S. PATENT DOCUMENTS

| 4,487,808 | A | | 12/1984 | Lambert ................... 428/423.1 |
|---|---|---|---|---|
| 5,306,798 | A | | 4/1994 | Horn et al. ...................... 528/58 |
| 5,576,072 | A | * | 11/1996 | Hostettler et al. ............ 427/532 |
| 6,020,071 | A | | 2/2000 | Watson ...................... 428/423.1 |
| 6,054,504 | A | * | 4/2000 | Dalla Riva Toma .......... 523/122 |
| 6,265,016 | B1 | * | 7/2001 | Hostettler et al. ........... 427/2.11 |

FOREIGN PATENT DOCUMENTS

| JP | 60-259269 | | 12/1985 |
|---|---|---|---|
| JP | 05-076590 | | 3/1993 |
| JP | 05-168695 | | 7/1993 |
| JP | 05-239176 | | 9/1993 |
| JP | 08-033704 | | 2/1996 |
| JP | 10-127647 | | 5/1998 |
| JP | 10-231347 | | 9/1998 |
| JP | 11-022613 | | 1/1999 |
| JP | 11506375 | A | 2/2000 |
| JP | 2002-128858 | | 5/2002 |
| JP | 2003-225301 | | 8/2003 |
| WO | WO 96/09086 | * | 3/1996 |
| WO | 96/39204 | | 12/1996 |

* cited by examiner

*Primary Examiner* — Ellen McAvoy
*Assistant Examiner* — Latosha Hines
(74) *Attorney, Agent, or Firm* — Kratz, Quintos & Hanson, LLP

(57) ABSTRACT

A lubricant surface coating having good lubricity and high durability, comprising (A) an urethane polymer layer comprising (a) 40 to 80% by weight of at least one component selected from an aromatic diisocyanate, an aliphatic diisocyanate and an alicyclic diisocyanate and (b) 20 to 60% by weight of a polyol having at least trifunctionality and (B) a hydrophilic polymer layer provided as the outer layer for the urethane polymer layer which comprises a polyalkylene glycol and/or a monomethoxypolyalkylene glycol; and a medical device having the surface coating.

6 Claims, No Drawings

WET LUBRICANT SURFACE COATING HAVING EXCELLENT DURABILITY, METHOD FOR SURFACE COATING, AND A MEDICAL DEVICE HAVING THE SURFACE COATING

BACKGROUND OF THE INVENTION

1. Field of the Invention

The present invention relates to surface coatings having high durability and showing good wet-lubricity; methods for surface coating; and medical devices having the same.

2. Related Background Art

Hitherto, surface coatings having wet-lubricity have been applied to medical devices having parts which are brought into contact with living bodies in various methods, in order to reduce pain and injury to the living bodies. However, since these surface coatings having the wet-lubricity generally have low affinity for materials forming medical devices, they have disadvantages that they dissolve or are peeled off in living bodies.

For improving this, there is, for example, a method in which a material surface is treated with ozone to generate functional groups on the substrate surface, followed by graft-polymerization of s hydrophilic polymer onto the substrate, as disclosed in Japanese Unexamined Patent Application Publication No. 5-76590; or a method performing a plasma treatment, as disclosed in Japanese Unexamined Patent Application Publication No. 5-168695. The methods, however are not so preferable because they have side effects such that durability is low and mechanical properties of the substrate are lowered.

Also, as disclosed in Japanese Unexamined Patent Application Publication No. 8-33704, a method in which a polymerization of a monomer is performed in the presence of a hydrophilic polymer compound to produce a second polymer compound, and an interpenetrating mesh structure of the two kinds of the polymer compounds is formed on a substrate surface, has been proposed, but the method has disadvantages that the substrate is deteriorated, and remaining monomers and oligomers elute.

Further, a method in which hydrophilic polymer is blended with a urethane resin having adhesion with a substrate, as disclosed in Japanese Unexamined Patent Application Publication No. 11-22613; and a method in which a urethane resin having a hydrophilic backbone is used, as disclosed in National Publication of International Patent Application No. 11-506375, have an issue to be solved that the adhesion with a substrate or wet-lubricity is not satisfied, though the lowering of the physical properties of substrates can be avoided. As a method for immobilizing a water-soluble polymer substrate on a substrate surface using an isocyanate group-containing compound, a method in which a solution including an isocyanate group-containing compound is coated, followed by binding a water-soluble polymer substance, as shown in Japanese Unexamined Patent Application Publication No. 60-259269; and a method in which a substrate is coated with a hydrophilic polymer whose terminals are isocyanated with a thermally decomposable blocked isocyanate, as shown in Japanese Unexamined Patent Application Publication No. 10-231347 are proposed. According to these methods, however, sufficient durability and lubricity cannot be obtained yet. In addition, as shown in U.S. Pat. No. 4,487,808, they are not suitable for use in medical devices whose substrate is thin and whose mechanical properties are remarkably changed due to heat history, such as, particularly, balloon catheters, because a heat treatment is required to immobilize the isocyanate group-containing compound to be coated, and the like. Also, substrates having no active hydrogen on their surfaces have insufficient durability, too.

In order to overcome the disadvantages, as disclosed in Japanese Unexamined Patent Application Publication No. 2003-225301, a method in which a substrate is swollen with a solvent, with which a urethane resin is acted, is proposed. Even this method has a disadvantage that the substrates are restricted, and mechanical properties of the substrate are affected.

DISCLOSURE OF THE INVENTION

Problems to be Solved by the Invention

An object of the present invention is to provide a surface coating having satisfactory wet-lubricity as well as having high durability, which surface coating is applicable to substrates having no specific functional groups on their surface.

Another object of the present invention is to provide a medical device having the above-mentioned surface coating; a method for surface-coating; a surface coating produced by the method for surface-coating; and a medical device having the surface coating.

Means to Solve the Invention

In view of such a circumstance, the present inventors have repeated intense studies. As a result, it has been found that the above-mentioned problems can be solved by adopting the following structures.

That is, the present invention relates to a surface coating having wet-lubricity, including: (A) a urethane polymer layer which includes (a) 40 to 80% by weight of at least one component selected from an aromatic diisocyanate, an aliphatic diisocyanate and an alicyclic diisocyanate and (b) 20 to 60% by weight of a polyol having at least trifunctionality, and (B) a hydrophilic polymer layer which is provided as an outer layer for the urethane polymer layer and which includes a polyalkylene glycol and/or a monomethoxypolyalkylene glycol.

Also, the present invention relates to the surface coating having wet-lubricity according to claim 1, wherein the polyalkylene glycol and/or monomethoxypolyalkylene glycol constituting the hydrophilic polymer layer (B) is a linear polyalkylene glycol and/or monomethoxypolyalkylene glycol having a weight average molecular weight of 1000 to 100000, or is a polyfunctional polyalkylene glycol derivative satisfying the formula:

$$50000 \times n > \text{weight average molecular weight} > 500 \times n \quad \text{(formula)}$$

wherein n is the number of hydroxyl terminal groups.

In addition, the present invention relates to a method for coating a surface coating having wet-lubricity which includes steps of: coating a mixed solution including an isocyanate compound and a polyol on a surface to form a urethane polymer layer; and then coating a solution including a polyakylene glycol and/or a monomethoxypolyalkylene glycol.

Further, the present invention provides a medical device having the above-mentioned surface coating.

Effects of the Invention

The lubricant surface coatings of the present invention can be produced easily, and have excellent wet-lubricity and high durability.

According to the present invention, medical devices having a surface coating with excellent wet-lubricity and high durability can be obtained from any kinds of materials. In the present invention, excellent wettability can be evaluated by a little change in coefficient of friction, as stated in Examples mentioned below.

DETAILED DESCRIPTION OF THE INVENTION

The present invention will be described in detailed below.

The wet-lubricant surface coatings of the present invention have a three-layer structure including 2 polymer layers on the surface of a substrate. Of the polymer layers, an inner layer close to the substrate is a urethane polymer layer (A), and an outer layer far from the substrate which is exposed on the surface is a hydrophilic polymer layer (B).

In the present invention, a thickness of each layer is not particularly limited, but when it is used for a medical device, the urethane polymer layer (A) has a thickness of 0.5 to 30 [μ], preferably from 0.5 to 10 [μ], more preferably from 0.5 to 5 [μ]. When the thickness of the urethane polymer layer (A) is too thin, the durability of the wet-lubricant surface coating is low when it is applied to friction, and when it is too thick, the mechanical properties of the substrate are impaired, and such ranges are undesirable.

When the coatings are used for medical devices, the hydrophilic polymer layer (B) has a thickness of 0.5 to 30 [μ], preferably from 0.5 to 10 [μ], more preferably from 0.5 to 5 [μ]. When the thickness of the hydrophilic polymer layer (B) is too thin, the lubricity is poor, and when it is too thick, eluted materials increase, and such ranges are undesirable.

In the present invention, the urethane polymer layer (A) is composed of (a) 40 to 80% by weight of at least one component selected from an aromatic diisocyanate, an aliphatic diisocyanate and an alicyclic diisocyanate, and (b) 20 to 60% by weight of a polyol having at least trifunctionality.

In the present invention, the aromatic diisocyanate, the aliphatic diisocyanate and the alicyclic diisocyanate refer to isocyanate compounds having 2 functional groups of isocyanate groups in their molecules, and the urethane polymer layer contains at least one kind of diisocyanate as listed above.

Examples of the aromatic diisocyanate may include 2,4-tolylene diisocyanate, 2,6-tolylene diisocyanate, 4,4'-diphenylmethane diisocyanate, p-phenylene diisocyanate, 3,3'-dimethylphenyl-4,4'-diisocyanate, meta-xylylene diisocyanate, dianisidine diisocyanate, m-xylene diisocyanate, tetramethylxylene diisocyanate, 1,5-naphthalene diisocyanate, and the like.

Examples of the aliphatic diisocyanate may include trans-vinylene diisocyanate, 2,2,4-trimethylhexamethylene diisocyanate, lysine diisocyanate, 1,6-hexamethylene diisocyanate, and the like are cited.

Example of the alicyclic diisocyanate may include trans-1,4-cyclohexane diisocyanate, cis-1,4-cyclohexane diisocyanate, 4,4'-dicyclohexylmethane diisocyanate, isophorone diisocyanate, and the like. These isocyanate compounds may be used alone or as a mixture thereof.

The content of the diisocyanate component (isocyanate compound) in the urethane polymer layer is 40% by weight or more and 80% by weight or less; preferably 45% by weight or more and 75% by weight or less; more preferably 50% by weight or more and 70% by weight or less. When the content of the isocyanate compound is less than 40% by weight, the adhesion with the substrate or the hydrophilic polymer layer thereof lowers, or a curing speed of the urethane resin becomes slow, which requires a heating treatment is required, thereby affecting the mechanical properties of the substrate, or which requires the addition of a catalyst generally used for controlling a curing speed such as an amine or tin compound, the catalyst being not preferable from the viewpoint of safety when it is used in living bodies. When the content of the isocyanate compound is more than 80% by weight, the obtained urethane resin is brittle.

The polyol having at least trifunctionality is used in combination with the isocyanate compound, for forming the urethane polymer layer. The term "polyol having at least trifunctionality" may include polyols having substantial trifunctionality. Also the term "polyol having at least trifunctionality" may include not more than difunctionality so long as its main component is a trifunctional polyol. When the polyol has not more than difunctionality, the adhesion with the urethane polymer layer lowers, and such a polyol is undesirable. In addition, when the polyol is water-soluble, it is undesirable to use it for a medical device such as a catheter which passes through a narrowing part, because the increase of the volume of the urethane polymer layer cased by swelling can interfere the passing.

Examples of the polyol having at least trifunctionality (hereinafter can be referred to as a "polyfunctional polyol") to form the urethane polymer layer may include branched polyol derivatives of such as polyester polyols, polyether polyols such as poly(oxypropylene ether) polyol and poly(oxyethylene-propylene ether) polyol, and acrylic polyol; castor oil and its derivatives; glycerol, trimethylol propane, trimethylol ethane, 1,2,6-hexane triol, pentaerythritol, sorbitol, mannitol, and the like. The branched polyol derivatives have a molecular weight of, preferably a range of 200 or more and 40000 or less, more preferably a range of 200 or more and 5000 or less, further more preferably a range of 200 or more and 3000 or less. When the molecular weight is more than 40000, the produced urethane polymer layer has a lowered adhesion, and such a range is undesirable. When the molecular weight is less than 200, the produced urethane polymer layer has lowered flexibility, and such a range is undesirable. These polyfunctional polyols may be used alone or as a mixture thereof.

Methods for forming the urethane polymer layer are not particularly limited, so long as urethane polymer layers within the range of the present invention can be obtained. Examples of the method may include a method in which a mixed suspension including an isocyanate compound (a) and a polyfunctional polyol (b) is brought into contact with the substrate surface to adsorb it on the substrate surface; a method in which a liquid wherein the above components are dissolved or suspended in a volatile organic solvent such as tetrahydrofuran, is coated or sprayed on the substrate surface by, for example, a dipping method, followed by allowing to stand to evaporate the volatile organic solvent, and simultaneously the isocyanate compound is reacted with the polyfunctional polyol to form a thin layer of a urethane polymer substrate on the substrate surface; and the like.

In this case, instead of the above-mentioned mixture of the isocyanate compound and the polyfunctional polyol, urethane prepolymers, which are previously produced by reacting the isocyanate compound with the polyfunctional polyol, can be used. The structures of the urethane prepolymers are not particularly limited so long as urethane polymers within the range of the present invention can be obtained therefrom. Examples of the isocyanate compound and the polyfunctional polyol may include those listed above. Also, reactants obtained by reacting a smaller amount of the polyfunctional polyol with the isocyanate compound, mixing the obtained urethane prepolymer with a remaining polyfunctional polyol, and further reacting the mixture, may be used.

The hydrophilic polymer layer (B) is provided on the urethane polymer layer as the outer layer, and is composed of the polyalkylene glycol and/or monomethoxypolyalkylene glycol, and if necessary, the polyfunctional polyalkylene glycol derivative, whereby the advantage that the durability of the surface coating is improved is provided. Examples of the polyalkylene glycol may include polyethylene glycol, polypropylene glycol, and the like. Examples of the monomethoxypolyalkylene glycol may include monomethoxypolyethylene glycol, monomethoxypolypropylene glycol, and the like. Examples of the polyfunctional polyalkylene glycol derivative may include tripolyethylene glycol ether of glycerine, tetrapolyethylene glycol ether of diglycerine, tetrapolyethylene glycol ether of pentaerythritol, and the like.

The polyalkylene glycols or the monomethoxypolyalkylene glycols have a weight average molecular weight of preferably 1000 to 100000, more preferably from 2000 to 50000. When the weight average molecular weight is less than 1000, the wet-lubricity is low, and when it is more than 100000, the surface of the coating is uneven or whitened, and such ranges are undesirable.

It is preferable that the polyfunctional polyalkylene glycol derivative has a weight average molecular weight within the range satisfying the following formula:

$$50000 \times n > \text{weight average molecular weight} > 500 \times n \qquad \text{(formula)}$$

wherein n is the number of hydroxyl terminal groups. When the weight average molecular weight is less than this range, the wet-lubricity is low, and when it is more than the range, the surface of the coating is uneven or whitened, and such ranges are undesirable.

Methods for forming the hydrophilic polymer layer are not particularly limited so long as hydrophilic polymer layers within the range of the present invention can be obtained. Examples of the method may include a method in which an aqueous polyalkylene glycol solution or dispersion is brought into contact with the above-mentioned substrate surface having the urethane polymer layer to adsorb it on the surface; a method in which a water-soluble polymer substance is dissolved or suspended in a volatile organic solvent such as ethanol, the obtained liquid is coated or strayed on the above-mentioned substrate surface having the urethane polymer layer by, for example, a dipping method, and drying it to form a thin layer of the hydrophilic polymer substrate on the above-mentioned substrate surface having the urethane polymer layer; and the like.

The surface coatings produced according to the present invention may be admixed with, in addition to the above-mentioned polymers and solvents, components having medicinal properties, anticoagulant agents, component having medicinal properties, disintegrants, promoters for absorbing the component having medicinal properties, plasticizers, stabilizers, ultra violet ray absorbers, and, if desired, various additives generally used in this art such as polymer compounds other than the above-mentioned.

Further, the top of the coating surfaces may be coated with hydrophobic oil such as silicone oil or functionalized silicone oil as an agent for protecting blocking.

Examples of the substrate to which the surface coating is applied may include, in addition to the medical devices, solid substrates contacting with water, for example, the surfaces of roof tiles, the surfaces of slate panels or plastic panels, inner walls of canals, swimming wears, rainwear, covering materials of boats and ships, and the like. In particular, the surface coatings of the present invention can be applied to precision devices, especially to medical devices, which are fine and are required hygienic maintenance. As the coatings have excellent appearance, high abrasion resistance and durability, the devices can maintain their inherent properties for a long period of time.

The term "medical device" used herein refers to a device which is used by bringing into contact with a body component such as a body tissue or body fluid. Examples of such a medical device may include, but not limited to, for example, blood bags, bags for urine collection, blood transfusion sets, surgical sutures, drain tubes, various catheters, blood accesses, blood circuits, artificial blood vessels, artificial kidney, artificial heart and lung, artificial valves, plasma exchange membranes, various adsorbents, continuous ambulatory peritoneal dialysis (CAPD) devices, intra-aortic balloon pomp (IABP), pacemakers, artificial joints, artificial bone head, dental materials, intraocular implants, soft contact lenses, various shunts, and the like.

Materials for the medical devices are not particularly limited, and polyalkylenes, polyamides, polyamide elastomers, polyesters, polycarbonates, polyurethanes, polyvinyl chloride, and silicone may be preferably used.

In these medical devices, all surfaces may have wet-lubricity, or only surfaces contacting with the body component such as body tissue or body fluid may have wet-lubricity. If desired, it is possible to produce two or more parts having different lubricity from the others by changing the coating amount by controlling the concentration or the number of times when coating is performed.

Examples of the method for applying the surface coating to devices such as the medical devices may include a method comprising the steps of: coating a mixed solution including the isocyanate compound and the polyol (polyfunctional polyol) on the surface of a device such as a medical device to from a urethane polymer layer; and then coating a solution including the polyalkylene glycol and/or monomethoxypolyalkylene glycol. Examples of the medium for the mixed solution and the like may include the mediums used in the formation of the urethane polymer layer (A) and the hydrophilic polymer layer (B).

According to such a coating method, the surface coatings having excellent appearance, sufficient wet-lubricity, and high durability can be applied to the precision devices such as the medical devices.

EXAMPLE

The present invention will be specifically described by means of Examples, but the invention is not limited thereto.

Abbreviations used in the description below depict the following substances.

4,4'-MDI: 4,4-diphenylmethane diisocyanate
2,4-TDI: 2,4-tolylene diisocyanate
PEG 20000: polyethylene glycol having a weight average molecular weight of 20000
PEG 4000: polyethylene glycol having a weight average molecular weight of 4000
PEG 500000: polyethylene glycol having a weight average molecular weight of 500000
MEPEG 4000: monomethoxypolyethylene glycol having a weight average molecular weight of 4000
PVA: completely saponificated polyvinyl alcohol having a weight average molecular weight of 2000
PVP K90: polyvinyl pyrrolidone K90
Pebax: polyamide elastomer resin made by Elf Atochem, Inc.
LDPE: low density polyethylene resin PI: polyimide, pyromellitic acid-4,4'-diaminophenyl ether copolymer Parts in Examples and Comparative Examples are parts by weight and "%" is "% by weight" unless otherwise specified. The measurements and evaluations in Examples and Comparative Examples were performed by the following procedures under the following conditions.

[Measurement of Coefficient of Friction and Durability]

Sliding was conducted using a hard vinyl chloride friction block having a diameter of 10 [mm] with a load of 100 [gf] at a speed of 100 [mm/sec] and a stroke of 30 [mm], through a friction tester (a surface property tester, "TRIBOGEAR TYPE-14DR") made by HEIDON. A coefficient of friction was measured after the above-mentioned procedure was repeated 10 times in both directions, and the durability was evaluated therefrom. Also a coefficient of friction was measured after the procedure was repeated 100 times of shuttling. The coefficient of friction after 100 times in both directions was compared with the coefficient of friction after 10 times in both direction, and the durability was evaluated as follows:

○: No change in the coefficient of friction.
Δ: The coefficient of friction was increased.
x: The coefficient of friction was increased to a value almost equal to or more than the value obtained before coating.

[Appearance]

The polymer layer was visually observed.
○: No uneven coating or whitening.
Δ: Slight uneven coating or whitening.
x: Remarkable uneven coating or whitening.

[SEM Observation]

A tube to which the coating was applied was cut into a ring, and the cut surface was observed with a scanning electron microscope. The thickness of the coating was evaluated.

Example 1

(1) Synthesis of a Polyurethane Prepolymer

A 10 L reactor was filled with the following substance.
4,4'-Diphenylmethane diisocyanate 70 parts
The content was heated to 70° C. under a nitrogen stream while stirring, and the following substance was continuously added dropwise thereto over 2 hours while stirring.
1,2,6-hexanetriol 30 parts
The mixture was stirred for further 2 hours at 70° C. under a nitrogen stream to give a polyurethane prepolymer (C-1).

(2) Synthesis of a Urethane Polymer Layer

The polyurethane prepolymer (C-1) 70 parts and castor oil 30 parts were dissolved in THF 300 parts and the mixture was thoroughly stirred to give a solution.

A Pebax tube having an outer diameter of 1 [mm] and a length of 200 [mm] was dipped in the solution, the tube was withdrawn lengthwise at a constant speed of 10 [mm/sec], and it was dried at room temperature for 1 hour to give a polyamide elastomer tube having a urethane polymer layer (A). The tube was cut perpendicularly to the length of the tube, and the cross-section was observed with a scanning electron microscope to measure a thickness of the coating. The thickness was 2.0 [mm].

(3) Production of a Hydrophilic Polymer Layer

To polyethylene glycol having a weight average molecular weight of 20000 10 parts was added 95% ethanol 90 parts, and the mixture was heated to 50° C. to dissolve.

The polyamide elastomer tube having the urethane polymer layer A) produced in (2) was dipped in the solution, the tube was withdrawn parallel in the long direction of the tube at a constant speed of 10 [mm/sec], and it was dried at room temperature for 12 hour to give a polyamide elastomer tube having a hydrophilic polymer layer (B). This tube was cut at a vertical surface to the long direction of the tube, and the cross-section was observed with a scanning electron microscope to measure a thickness of the coating. The thickness was 1.5 [mm]. The evaluation results of the obtained polyamide elastomer tube having the coating layers are shown in Table 2.

Examples 2 to 4

A polyurethane prepolymer (C-2), (C-3) or (C-4) was produced using starting materials shown in Table 1 in a similar procedure to Example 1. The prepolymer was combined with a polyalcohol shown in Table 2, and an elastomer tube having a urethane polymer layer was obtained in a similar procedure to Example 1, then, a hydrophilic polymer layer was formed. The evaluation results of the obtained polyamide elastomer tubes having the surface coating are shown in Table 2.

Examples 5 and 6

An elastomer tube having a urethane polymer layer was produced in the same manner as in Example 1 except that 4,4'-MDI and 2,4-TDI were used, as shown in Table 2, instead of the polyurethane prepolymer, and then a hydrophilic polymer layer was formed. The evaluation results of the obtained polyamide elastomer tubes having the surface coating are shown in table 2.

Examples 7 and 8

A coating layer was formed on the urethane polymer layer in the same manner as in Example 1 except that a concentration of a THF solution including the polyurethane prepolymer and polyalcohol was changed to one shown in Table 2, when the urethane polymer layer was formed. The evaluation results of the polyamide elastomer tubes having the surface coating are shown in Table 2.

Example 9

An elastomer tube having a urethane polymer layer was obtained in the same manner as in Example 2 except that the hydrophilic polymer substance was changed into PEG 4000, as shown in Table 2, and then a hydrophilic polymer layer was formed. The evaluation results of the obtained polyamide elastomer tube having the surface coating are shown in Table 2.

Examples 10 to 13

A coating layer was formed on the surface of a substrate shown in Table 2 in the same manner as in Example 2. The evaluation results of the obtained tubes having the surface coating are shown in Table 2.

Comparative Examples 1 and 9

A Pebax tube having a surface coating was obtained in the same manner as in Example except that the urethane polymer layer was formed in a ratio shown in Table 3. The evaluation results of the obtained tubes having the surface coating are shown in Table 3.

Comparative Examples 2, 3, 7 and 8

A urethane polymer layer was formed in the same manner as in Example except that a polyalcohol shown in Table 3 was used as the glycol, and then the hydrophilic polymer layer was formed to give a tube having the surface coating. The evaluation results of the obtained tube having the surface coating are shown in Table 3.

Comparative Examples 4, 5 and 6

A surface coating was formed in the same manner as in Example 2 except that a substance shown in Table 3 was used as the hydrophilic polymer substance. The evaluation results of the obtained tube having the surface coating are shown in Table 3.

TABLE 1

|  |  | Prepolymer | | | |
|---|---|---|---|---|---|
|  |  | (C-1) | (C-2) | (C-3) | (C-4) |
| Isocyanate [part] | 4,4'-MDI | 70 | 67 | | |
|  | 2,6-TDI | | | 70 | |
|  | 1,6-HDI | | | | 50 |
| Polyol [part] | 1,2,6-hexanetriol | 30 | | | |
|  | Castor oil | | 33 | 30 | 50 |

TABLE 2

| | | | Ex. 1 | Ex. 2 | Ex. 3 | Ex. 4 | Ex. 5 | Ex. 6 | Ex. 7 |
|---|---|---|---|---|---|---|---|---|---|
| Substrate | | | Pebax | Pebax | Pebax | Pebax | Pebax | Pebax | Pebax |
| Urethane polymer layer (A) | Isocyanate compound [part] | Prepolymer (c-1) | 70 | | | | | | |
| | | Prepolymer (c-2) | | 80 | | | | | 80 |
| | | Prepolymer (c-3) | | | 90 | | | | |
| | | Prepolymer (c-4) | | | | 90 | | | |
| | | 4,4'-MDI | | | | | 55 | | |
| | | 2,6'-TDI | | | | | | 75 | |
| | Polyalcohol (poly-functional polyol) [Part] | 1,2,6-hexanetriol | 30 | | | | | | |
| | | Castor oil | | 20 | 10 | 10 | 45 | | 20 |
| | | Trimethylol propane | | | | | | 25 | |
| | THF solution concentration | | 25% | 25% | 25% | 25% | 30% | 40% | 40% |
| | Isocyanate compound/polyfunctional polyol compound ratio | | 49/51 | 53.6/46.4 | 63/27 | 45/55 | 55/45 | 75/25 | 53.6/46.6 |
| | Thickness of coating layer [μ] | | 2.0 | 1.5 | 1.5 | 1.5 | 1.2 | 2.0 | 4.0 |
| Hydrophilic polymer layer (B) | Hydrophilic polymer [part] | PEG20000 | 100 | 100 | 100 | 100 | 100 | 100 | 100 |
| | | PEG4000 | | | | | | | |
| | | MEPEG4000 | | | | | | | |
| | EtOH solution concentration | | 10% | 10% | 10% | 10% | 10% | 15% | 15% |
| | Thickness of coating layer [μ] | | 1.5 | 1.5 | 1.0 | 2.0 | 2.0 | 2.0 | 2.0 |
| Appearance | | | ○ | ○ | ○ | ○ | ○ | ○ | ○ |
| Friction resistance value | | | 0.03 | 0.04 | 0.03 | 0.03 | 0.04 | 0.04 | 0.02 |
| Durability | | | ○ | ○ | ○ | ○ | ○ | ○ | ○ |

| | | | Ex. 8 | Ex. 9 | Ex. 10 | Ex. 11 | Ex. 12 | Ex. 13 |
|---|---|---|---|---|---|---|---|---|
| Substrate | | | Pebax | Pebax | LDPE | PI | SUS 304 | SUS 304 |
| Urethane polymer layer (A) | Isocyanate compound [part] | Prepolymer (c-1) | | | | | | |
| | | Prepolymer (c-2) | 80 | 80 | 80 | 80 | 80 | 80 |
| | | Prepolymer (c-3) | | | | | | |
| | | Prepolymer (c-4) | | | | | | |
| | | 4,4'-MDI | | | | | | |
| | | 2,6'-TDI | | | | | | |
| | Polyalcohol (poly-functional polyol) [Part] | 1,2,6-hexanetriol | | | | | | |
| | | Castor oil | 20 | 20 | 20 | 20 | 20 | 20 |
| | | Trimethylol propane | | | | | | |
| | THF solution concentration | | 10% | 25% | 25% | 30% | 35% | 25% |
| | Isocyanate compound/polyfunctional polyol compound ratio | | 53.6/46.6 | 53.6/46.6 | 53.6/46.6 | 53.6/46.6 | 53.6/46.6 | 53.6/46.6 |
| | Thickness of coating layer [μ] | | 1.5 | 2.0 | 2.0 | 2.0 | 3.0 | 2.5 |
| Hydrophilic polymer layer (B) | Hydrophilic polymer [part] | PEG20000 | 100 | | 100 | 100 | 50 | |
| | | PEG4000 | | 100 | | | 50 | |
| | | MEPEG4000 | | | | | | 100 |
| | EtOH solution concentration | | 10% | 10% | 15% | 20% | 10% | 10% |
| | Thickness of coating layer [μ] | | 2.0 | 2.0 | 4.0 | 7.5 | 1.5 | 1.5 |
| Appearance | | | ○ | ○ | ○ | ○ | ○ | ○ |
| Friction resistance value | | | 0.08 | 0.08 | 0.08 | 0.10 | 0.07 | 0.10 |
| Durability | | | ○ | ○ | ○ | ○ | ○ | ○ |

TABLE 3

| | | | Com. Ex. 1 | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|---|---|---|
| Substrate | | | Pebax | LDPE | PI | Pebax | Pebax | Pebax | Pebax | SUS304 | Pebax |
| Urethane polymer layer (A) | Isocyanate compound | Prepolymer (c-2) | 40 | 60 | | 80 | 80 | 80 | 80 | | |
| | | 4,4'-MDI | | | 40 | | | | | 60 | 85 |
| | Polyalcohol [part] | Castor oil | 60 | | | 20 | 20 | 20 | | | 15 |
| | | 1,6-hexanediol | | 40 | | | | | 20 | | |
| | | glycerin | | | 60 | | | | | 40 | |
| | THF solution concentration | | 25% | 25% | 25% | 25% | 25% | 25% | 25% | 25% | 25% |
| | Isocyanate compound/polyol compound ratio | | 26.8/73.2 | 40/60 | 40/60 | 53.6/46.6 | 53.6/46.6 | 53.6/46.6 | 53.6/46.6 | 60/40 | 85/15 |
| | Isocyanate compound/ polyfunctional polyol compound ratio | | 26.8/73.2 | 40/20 | 40/0 | 53.6/46.6 | 53.6/46.6 | 53.6/46.6 | 53.6/26.6 | 60/0 | 85/15 |
| | Thickness of coating layer [μ] | | 2.0 | 2.0 | 1.5 | 1.5 | 1.5 | 1.5 | 1.5 | 1.2 | 1.0 |
| Hydrophilic polymer layer (B) | Hydrophilic polymer [part] | PEG20000 | 100 | 100 | 100 | | | | | | |
| | | PEG4000 | | | | | | | 100 | 100 | 100 |
| | | PEG500000 | | | | 100 | | | | | |
| | | PVA20000 | | | | | | 100 | | | |
| | | PVP K90 | | | | | 100 | | | | |
| | EtOH solution concentration | | 10% | 15% | 20% | 10% | 10% | 10% | 10% | 10% | 10% |
| | Thickness of coating layer [μ] | | 1.5 | 3.0 | 8.0 | 2.0 | 2.0 | 2.0 | 2.0 | 2.0 | 8.0 |
| Appearance | | | ○ | ○ | ○ | X | ○ | Δ | ○ | Δ | ○ |
| Friction resistance value | | | 0.05 | 0.08 | 0.09 | 0.04 | 0.10 | 8.20 | 12.00 | 10.00 | 0.05 |
| Durability | | | Δ | Δ | X | ○ | Δ | X | X | X | X |

As apparent from the results of Tables 2 and 3, the lubricity surface coatings of the present invention, represented by Examples 1 to 13, shows excellent wet-lubricity and high durability. It is clear that even if the substrate does not have active hydrogen or specific functional groups on its surface, excellent lubricity and high durability are shown.

INDUSTRIAL APPLICABILITY

The surface coatings of the present invention are preferably used in solid substrates contacting with water, especially, medical devices such as blood bags, bags for urine collection, blood transfusion sets, surgical sutures, drain tubes, various catheters, blood accesses, blood circuits, artificial blood vessels, artificial kidney, artificial heart and lung, artificial valves, plasma exchange membranes, various adsorbents, CAPD, IABP, pacemakers, artificial joints, artificial bone heads, dental materials, intraocular implants, soft contact lenses, and various shunts.

What is claimed is:

1. A surface coating having wet-lubricity, comprising:
an inner layer on the surface that is:
(A) a urethane polymer layer which includes (a) 40 to 80% by weight of at least one component selected from an aromatic diisocyanate, an aliphatic diisocyanate and an alicyclic diisocyanate and (b) 20 to 60% by weight of a polyol having at least trifunctionality for forming the urethane polymer layer, said polyol being selected from the group consisting of branched polyol derivatives of polyester polyols, polyether polyols (poly(oxypropylene ether) polyol and poly(oxyethylene-propylene ether) polyol), and acrylic polyol; castor oil and its derivatives; glycerol, trimethylol propane, trimethylol ethane, 1,2,6-hexane triol, pentaerythritol, sorbitol, and mannito, and
an outer layer formed on said inner layer that is:
(B) a hydrophilic polymer layer which is provided as an outer layer for the urethane polymer layer and which includes a polyalkylene glycol and/or a monomethoxypolyalkylene glycol, such that said surface coating has both wet lubricity and durability.

2. The surface coating having wet-lubricity according to claim 1, wherein the polyalkylene glycol and/or monomethoxypolyalkylene glycol constituting the hydrophilic polymer layer (B) is a linear polyalkylene glycol and/or monomethoxypolyalkylene glycol having a weight average molecular weight of 1000 to 100000; or a polyfunctional polyalkylene glycol derivative satisfying the formula:

$$50000 \times n > \text{weight average molecular weight} > 500 \times n \quad \text{(formula)}$$

wherein n is the number of hydroxyl terminal group(s).

3. A medical device having the surface coating according to claim 1 or 2.

4. A method for coating which provides a surface coating comprising the steps of
forming an inner first layer by coating a mixed solution including an isocyanate compound and a polyol having at least trifunctionality on a surface to form a urethane polymer layer;
coating a solution including a polyalkylene glycol and/or a monomethoxypolyalkylene glycol; and then
forming a hydrophilic polymer layer, as a second layer on said first layer, which is provided as an outer layer for the urethane polymer layer, such that said surface coating has both wet lubricity and durability.

5. A surface coating produced by the method for coating according to claim 4.

6. A medical device having the surface coating according to claim 5.

* * * * *